United States Statutory Invention Registration [19]

[11] Reg. Number: H791

Katsuyama et al. [43] Published: Jun. 5, 1990

[54] MULTILAYER ANALYTICAL ELEMENT FOR QUANTITATIVE ANALYSIS OF BILIRUBIN

[76] Inventors: Harumi Katsuyama; Shigeki Kageyama; Shigeru Nagatomo, all c/o Fuji Photo Film Co., Ltd., 3-11-46, Senzui, Asaka-shi, Saitama, Japan

[21] Appl. No.: 106,906

[22] Filed: Oct. 8, 1987

Related U.S. Application Data

[63] Continuation of Ser. No. 590,730, Mar. 19, 1984, abandoned.

[30] Foreign Application Priority Data

Mar. 18, 1983 [JP] Japan ..... 58-45547

[51] Int. Cl.[5] ..... G01N 21/78; G01N 33/72

[52] U.S. Cl. ..... 422/56; 436/97; 436/170; 436/178; 436/903

[58] Field of Search ..... 422/56, 57, 58; 436/97, 436/169, 170, 178, 903

[56] References Cited

U.S. PATENT DOCUMENTS

| | | | |
|---|---|---|---|
| Re. 30,267 | 5/1980 | Bruschi | 436/903 X |
| 2,854,317 | 9/1958 | Free et al. | 436/97 |
| 3,802,842 | 4/1974 | Lange et al. | 436/169 |
| 4,038,031 | 7/1977 | Lam | 436/903 X |
| 4,069,017 | 1/1978 | Wu et al. | 422/56 X |
| 4,160,008 | 7/1979 | Fenocketti et al. | 422/56 |
| 4,190,419 | 2/1980 | Bauer | 436/97 |
| 4,376,828 | 3/1983 | Rupchock et al. | 436/178 X |
| 4,405,711 | 9/1983 | Masuda et al. | 422/56 X |
| 4,468,467 | 8/1984 | Babb et al. | 436/97 |
| 4,604,347 | 8/1986 | Arai et al. | 422/57 X |

*Primary Examiner*—John F. Terapane
*Assistant Examiner*—Daniel Metzmaier

[57] ABSTRACT

A multilayer analytical element for quantitative analysis of bilirubin in a liquid sample by a diazo method, which comprises a laminated structure consisting essentially of:

(1) a porous reagent layer containing an acidic binder and a diazonium salt being reactive to bilirubin to produce azobilirubin;
(2) an absorbent layer capable of absorbing an excessive liquid portion; and
(3) a liquid-impermeable light-transmissive support.

8 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MULTILAYER ANALYTICAL ELEMENT FOR QUANTITATIVE ANALYSIS OF BILIRUBIN

This is a continuation of application Ser. No. 590,730, filed Mar. 19, 1984, now abandoned.

BACKGROUND OF THE INVENTION

1. Field of the Invention

The present invention relates to a multilayer analytical element for quantitative analysis of bilirubin, and more particularly to a multilayer analytical element employable for quantitative analysis of bilirubin based on a dry system with high accuracy by a simple and quick operation.

2. Description of Prior Arts

Bilirubin, a principal component of a bile pigment in a body fluid, is produced in serum by decomposition of heme originating from hemoglobin in red blood corpuscle. Bilirubin is then absorbed by a liver, in which bilirubin is converted to a glucuronic acid-conjugated product, etc. and excreted in bile. The content of bilirubin in blood increases in response to increase of decomposition of hemoglobin as well as decrease of the liver function. Accordingly, the quantitative analysis of bilirubin is considered to be an indispensable test item in the clinical test.

As the method for quantitative analysis of bilirubin in serum, there are known a quantitative analysis method comprising photometric measurement of the yellow color inherently provided to the bilirubin, and a colorimetric analysis of red azobilirubin produced by coupling reaction of bilirubin and diazotized sulfanilate (p-sulfobenzenediazonium salt, Ehrlich reagent) based on Ehrlich reaction discovered by Van den Bergh. The latter method is generally named a diazo method.

Details of methods for quantitative analysis of bilirubin in serum are described in "Comprehensive Text of Clinical Test Technology" edited by Ishii, Vol. 6, pp. 332–350 (Igaku Shoin, 1975).

Details of the diazo method are further described below.

Bilirubin produced in serum by the decomposition of heme is named free bilirubin. This bilirubin is as such hydrophobic, but is dissolved in serum in combination with serum albumin, in the form of being adsorbed by the serum alubmin. The free bilirubin introduced into liver is combined with glucuronic acid through a covalent bond to become conjugated with glucuronic acid. Thus, a glucuronic acid-conjugated bilirubin which is improved in the water-solubility by the aid of the hydrophilic group contained in the glucuronic acid is produced. Also known is a highly water-soluble bilirubin combined to serum albumin, while no production mechanism is known on this product (J. J. Lauff, et al., Clinical Chemistry, 28(4), 629–637 (1982)).

Among these various bilirubins, the highly water-soluble conjugated bilirubin and the albumin-conjugate bilirubin both easily react with a diazonium salt, and are directly subjected to colorimetry. Accordingly, these bilirubins are named direct bilirubins.

The hydrophobic free bilirubin undergoes coupling reaction in the presence of a reaction accelerator such SO as caffeine, sodium benzoate, sodium acetate, dyphylline (C. A. Registory No. [479-18-5]), urea, a nonionic surfactant, gum arabic, an alcohol (e.g., methanol, ethanol), an acid amide, sulfoxide, etc., to produce azobilirubin. Therefore, the quantitative analysis of free bilirubin is generally performed indirectly by a stage of colorimetrically determining the total bilirubin content in a liquid sample in the presence of a reaction accelerator and a subsequent stage of subtracting the direct bilirubin content determined separately in the absence of a react±on accelerator from the total bilirubin content. For this reason, the free bilirubin is otherwise named an indirect bilirubin.

Details of the diazo method for quantitative analysis of bilirubin are described in the following publications: M. Michaelsson, Scand. J. Clin. Lab. Invest., 13 (Suppl.), 1–80 (1961); H. Malloy, J. Biol. Chem., 119, 481(1939); and Z. K. Shihabi, et al., American Journal of Medical Technology, 43(10), 1004–1007(1977).

A great number of analytical processes for quantitative analysis of bilirubin based on the above-mentioned diazo method employing a multilayer analytical element have been proposed, for instance, in Japanese Patent Publication No. 53(1978)-28119, and Japanese Patent Provisional Publications Nos. 54(1979)-33094, 55(1980)- 44492, 56(1981)-10255, 56(1981)-30503, and 57(1982)-23859.

On the other hand, a number of studies on improvement of the analytical accuracy of a multilayer analytical element for quantitative analysis of bilirubin by way of utilizing a non-fibrous isotropically porous spreading layer have been already made and described in Japanese Patent Publication No. 57(1982)-25783 and Japanese Patent Provisional Publications Nos. 53(1978)-89797, 57(1982)-37262 and 57(1982)-110942. It is noted, however, that all of the multilayer analytical elements for quantitative analysis of bilirubin employing an isotropically porous spreading layer described in these publications are not based on the above-mentioned diazo method, but based on other quantitative analytical systems. Further, these known multilayer analytical elements have such drawback that non-diffusive bilirubins such as protein-conjugated bilirubin is not detectable, and accordingly the total bilirubin content is not appropriately analyzed by these analytical elements.

SUMMARY OF THE INVENTION

A primary object of the present invention is to provide a multilayer analytical element utilizing the diazo method which is employable for quantitatively analyzing the total bilirubin content. In more detail, the present invention provides a multilayer analytical element for highly sensitive quantitative analysis of bilirubin which enables a non-migratory non-diffusive bilirubin to sufficiently diffuse within a porous reagent layer so as to efficiently undergo a coupling reaction with a diazonium salt contained therein.

Another object of the invention is to provide a multilayer analytical element in which the diazonium salt is protected by an acidic binder to improve preservability and stability of the diazonium salt.

A further object of the invention is to provide a multilayer analytical element showing high-color formation and high-stability in which the coupling reaction can be stably buffered without lowering the preservability and stability of the diazonium salt.

There is provided by the present invention a multilayer analytical element for quantitative analysis of bilirubin in a liquid sample by a diazo method, which comprises a laminated structure consisting essentially of:

(1) a porous reagent layer containing an acidic binder and a diazonium salt being reactive to bilirubin to produce azobilirubin;

(2) an absorbent layer capable of absorbing an excessive liquid portion; and (3) a liquid-impermeable light-transmissive support.

In the present invention, the term "absorbent layer" means a layer capable of absorbing an aqueous medium, aqueous solution or the like.

DETAILED DESCRIPTION OF THE INVENTION

As described hereinbefore, a total bilirubin content is difficultly determined by the use of a conventional multilayer analytical element because a portion of bilirubin is hardly detected by the conventional element. The present invention provides a multilayer analytical element capable of quantitatively analyzing the total bilirubin content.

Bilirubin is generally present in the form of being absorbed by a serum albumin or in the form of being combined with a serum albumin. If an analytical element having a polymer film disturbing permeation of the serum albumin laminated thereon is employed for the analysis, the serum is required to be processed with a dissociating agent for separating bilirubin from the albumin such as cafeine, sodium benzoate, or sodium acetate in advance of the analysis. For this reason, the conventional multilayer analytical element for this purpose contains the dissociating agent in the spreading layer. Nevertheless, the dissociating agent is not effective for dissociating a bilirubin conjugated with albumin through covalent bonding, and therefore the migration and diffusion of the conjugated bilirubin cannot be improved.

Accordingly, in order to quantitatively analyzing an analyte having a relatively high molecular weight or an analyte having a hydrophobic molecular structure such as bilirubin, total protein, albumin, or globulin, such analyte should be converted into chemical species which can easily migrate or diffuse into a reagent layer containing a detection reagent and can produce a detectable signal upon reaction with the detection reagent.

It is known that in the case of analyzing a low molecular weight analyte by means of the conventional analytical element, i.e., an analytical element consisting essentially of a reagent layer (e.g., filter paper, non woven fabrics, glass fiber sheet) containing a diazonium salt (detection reagent) and a non-absorbent support, a color formation cf high optical density can be accomplished by restricting the applied sample volume to a level not exceeding the void volume of the element. However, if the analyte is non-diffusive, the color formation is not sufficient regardless of varying the applied sample volume.

According to the present invention, the drawbacks of the conventional analytical element brought about by the non-diffusiveness of the analyte is obviated by the provision of the absorbent layer to the analytical element, whereby making it possible to produce high colorformation. The absorbent layer of the invention serves to absorb a solvent (i.e., liquid medium) of a liquid sample without accepting an analyte in the liquid sample to elevate the concentration of the analyte diffusing into the reagent layer, thereby enhancing the efficiency of the reaction between a high molecular weight analyte (e.g., bilirubin, albumin, etc.) and a detection reagent.

The absorbent layer is constituted by a material comprising a hydrophilic polymer as a main component. The hydrophilic polymer preferably contains a group capable of attracting and retaining the introduced water or aqueous medium within the absorbent layer through strong hydrogen bond, preferably has a degree of swelling at a high level, and is preferably water-insoluble.

The degree of swelling of the absorbent layer preferably ranges from approx. 1.5 to approx. 30 times, more preferably from approx. 2.5 to approx. 20 times, as much as the original volume. In the specification, the term "degree of swelling" means a ratio of thickness of a wetted layer to a dry layer, in which the thickness of the wetted layer is measured upon reaching an equilibrium state after swelling the dry layer with water at 30° C. on a polyethylene terephthalate support.

The hydrophilic polyer employable for the formation of or incorporation into the absorbent layer can be a non-porous polymer capable of absorbing and retaining water because of its swelling property or other properties, or a polymer containing cross-linked molecular chains capable of absorbing and retaining water of its microporous structure showing swelling property.

Examples of the hydrophilic polymer satisfying the above-described conditions include natural polymers or their crosslinked products such as gelatin, dextran, starch, and modified starch; homopolymers and copolymers of hydrophilic monomers such as hydroxyethyl acrylate, hydroxyethyl methacrylate, N-(hydroxyalkyl-)acrylamide and copolymers of the acrylamide with one or more of the above-mentioned monomers, in which the homopolymer and copolymer can be modified through crosslinking. Most preferred is gelatin.

The degrees of some hydrophilic polymers are given below.

| | |
|---|---|
| Unhardened gelatin | approx. 6–7 |
| Hardened gelatin | approx. 3–4 |
| hydroxyethyl-modified agarose | approx. 1.5 |
| Dextran | approx. 2 |
| Crosslinked polyacrylamide/agarose | approx. 17 |
| Polyhydroxyethyl acrylate/acrylamide gel | approx. 15 |
| Crosslinked polyviyl alcohol | approx. 3–15 |

The absorbent layer of the present invention preferably contains a basic polymer therein. The basic polymer contained in the absorbent layer can adjust pH of the reagent layer in conjunction with the acidic binder (i.e., acidic polymer) contained in the porous reagent layer, to buffer the surrounding condition of the reaction between an analyte and a diazonium salt. Accordingly, the multilayer analytical element of the invention is further improved in the quantitative accuracy.

Examples of the basic polymer employable for the above-mentioned purpose include:

a homopolymer of an unsaturated monomer selected from the group consisting of 2-vinylpyridine, 4-vinylpyridine, N-vinylimidazole, 1-vinyl-3-alkyl-2,3-dihydroimidazole (i.e., 1-vinyl-3-alkyl-4-imidazoline, preferably, 1-vinyl-3-ethyl-2,3-dihydroimidazole, 1-vinyl-3-methyl-2,3-dihydroimidazole, 1-vinyl-3-benzyl-2,3-dihydroimidazole, etc.), 2-vinyl-1-alkyl-imidazole (preferably, 2-vinyl-1-methylimidazole, 2-vinyl-1-ethylimidazole, 2-vinyl-1-benzylimidazole, etc.), (dialkylamino)alkyl acrylate (preferably, β-(dimethylamino)-methyl acrylate, β-(dimethylamino)ethyl acrylate, β-(diethylamino)ethyl acrylate, β-morpholinoethyl acrylate, γ-(dimethylamino)propyl acryalte, etc.), (dialkylamino)alkyl methacrylate (preferably, β-(dimethylamino)methyl methacrylate, β-(dimethylamino)ethyl methacrylate, β-(dimethylamino)ethyl methacrylate, β-morpholinoethyl methacrylate, γ-(dimethylamino)propyl methacryalte, etc.), N -[(dialkylamino)alkyl]acrylamide (preferably, N-[(dimethylamino)propyl]acrylamide, etc.), and N-/(dialkylamino)alkyl]methacrylamide (preferably, N-[(dimethylamino)propyl]methacrylamide, etc.);

a copolymer of said unsaturated monomer; or a copolymer of said unsaturated monomer and other unsaturated monomer than said unsaturated monomer.

Examples of the other unsaturated monomer include styrene, divinylbenzene, acrylamide, N-substituted acrylamide, methacylamide, N-substituted methacrylamide, acrylic acid esters, methacrylic acid esters, and N-vinylpirrolidone.

The basic polymer can be employed singly or in combination therewith. The basic polymer can be employed in combination with the aforementioned hydrophilic polymer such as gelatin.

The thickness of the absorbent layer preferably ranges from 3 to 50 μm, most preferably from 10 to 30 μm.

The material constituting a matrix of the porous reagent layer of the invention can be a material having voids allowing easy migration or diffusion of a high molecular weight analyte in and through the material. Examples of the material include filter paper, nonwoven cloth, woven cloth, glass fiber sheet (e.g., glass fiber filter), and membrane filter formed of blushed polymer. The porous reagent layer of the invention can be prepared by superposing, for instance, through pressing, the material of the porous reagent layer containing a diazonium salt capable of reacting with bilirubin to give azobilirubin and an acidic binder on the absorbent layer provided on a transparent support, to obtain an integrated structure.

The material employable for forming the matrix of the porous reagent layer of the invention is not restricted by the above-described materials For instance, non-fabric isotropically porous layer prepared by a coating method described in Japanese Patent Publication No. 53(1978)-21677 and U.S. Pat. No. 3,992,158 can be used.

Examples of the diazonium salt employable as the bilirubin detection reagent include a variety of diazonium salts being conventionally known in the art of quantitative analysis of bilirubin utilizing the wet and dry diazo methods.

Other examples of the diazonium salt employable in the invention include non-diffusive (i.e., anti-diffusive) aryldiazonium salt which contains in the aryl group (preferably a benzene ring) at least one substituent selected from the group consisting of an alkoxycarbonyl group, an alkylaminosulfonyl group and an alkylaminocarbonyl group (in which each of the alkyl and alkoxy preferably contains 2–22 carbon atoms), and preferably further contains at least one substituent selected from the group consisting of an alkyl group and an alkoxy group (in which each of alkyl and alkoxy preferably contains 1–12 carbon atoms.

Representative examples of the aryldiazonium salt are given below:

1: 2-methoxy-5-(tetradecyloxycarbonyl)benzenediazonium tetrafluoroborate,

2: 2-methoxy-5-(tetradecyloxycarbonyl)benzenediazonium hexafluoroborate,

3: 2-ethoxy-5-(hexadecyloxycarbonyl)benzenediazonium tetrafluoroborate,

4: 2-dodecyloxy-5-(ethoxycarbonyl)benzenediazonium tetrafluoroborate,

5: 2-methoxy-5-[β-(2′,4′-di-t-amylphenoxy)ethoxycarbonyl]benzenediazonium tetrafluoroborate, 6: 2-methoxy-5-(N-hexadecylsulfamoyl)benzenediazonium tetrafluoroborate, 7: 2-propoxy-5-(N-tetradecylsulfamoyl)benzenediazonium perchlorate, 8: 2-octyloxy-5-(N-decylsulfamoyl)benzenediazonium hexafluorophosphate, 9: 3,5-bis(dodecyloxycarbonyl)benzenediazonium tetrafluoroborate, 10: 3,5-bis(tetradecyloxycarbonyl)benzenediazonium tetrafluoroborate, 11: 2-methoxy-5-(N-tetradecylcarbomoyl)benzenediazonium tosylate, 12: 2-methoxy-5-[N-(4-t-amylphenoxyethyl)carbamoyl]benzenediazonium 1-naphthalenasulfonate, 13: 4-(hexadecyloxycarbonyl)benzenediazonium tetrafluoroborate, 14: 4-(N-hexadecylsulfamoyl)benzenediazonium tetrafluoroborate, 15: 3-hexadecylcarbonylbenzenediazonium tetrafluoroborate, 16: 3-(N-tetradecylcarbamoyl)benzenediazonium tetrafluoroborate, 17: 2-methyl-5-tetradecyloxycarbonylbenzenediazonium tetrafluoroborate, 18: 2-butyl-5-decyloxycarbonylbenzenediazonium tetrafluoroborate, 19: 4-{N-[γ-(2′,4′-di-t-amylphenoxy)propyl]carbamoyl}benzenediazonium tetrafluoroborate, and 20: 4-[β-(2′,4′-di-t-amylphenoxy)ethoxy]carbonylbenzenediazonium tetrafluoroborate.

In the case that the absorbent layer contains a basic polymer, the non-diffusive aryldiazonium salt is preferably employed as the bilirubin detection agent.

The acidic binder serves to keep the diazonium salt contained in the analytical element. In the case that a basic polymer is contained in the absorbent layer, the acidic binder serves to adjust pH of the reagent layer in conjunction with the basic polymer so as to buffer the reaction conditions for the reaction between an analyte and a diazonium salt.

Examples of the acidic polymer constituting the acidic binder include:

a homopolymer of unsaturated monomer selected from the group consisting of p-styrenesulfonic acid, acrylic acid, methacrylic acid, maleic acid, maleic anhydride, maleic acid monoamide, maleic acid monoester, N-(sulfoalkyl)acrylamide (preferably, N-(β-sulfo-t-butyl)acrylamide, etc.), and N-(sulfoalkyl)methacrylamide (preferably, N-(β-sulfo-t-butyl)methacrylamide, etc.);

a copolymer of said unsaturated monomer; or a copolymer of said unsaturated monomer and other unsaturated monomer than said unsaturated monomer.

Examples of the other unsaturated monomer are the same as those given hereinbefore for the basic polymer.

The acidic binder can be a polycarboxylic acid which contains a repeating unit of a divalent group derived from a compound having carboxyl groups and an ethylenic-unsaturated double bond, and the nonionic surface active agent is attached to at least a portion of the carboxyl groups through ester linkage.

In the polycarboxylic acid derivative binder, the divalent group derived from a compound having the repeating unit including the carboxyl group and ethylenic-unsaturated double bond preferably has the formula (I):

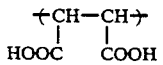

(I)

The polycarboxylic acid derivative binder employable in the invention can be obtained, for instance, in the following manner. A polycarboxylic acid is initially prepared. The so prepared polycarboxylic acid is caused to react with a nonionic surface active agent having a hydroxyl group in the molecule optionally in the presence of a catalyst, to perform an esterification reaction between a portion of a great number of the carboxyl groups contained in the polycarboxylic acid and a hydroxyl group of the nonionic surface active agent. Through the esterification reaction, a polycarboxylic acid derivative carrying a nonionic surface active agent attached to a portion of the carboxyl groups of the polycarboxylic acid is obtained.

Representative examples of the polycarboxylic acid include acrylic acid copolymers, methaorylic acid copolymers, maleic acid copolymers, copolymers of a maleic acid monoester such as monomethyl maleate, monoethyl maleate, monopropyl maleate, monobutyl maleate and monoamyl maleate, and itaconic acid copolymers and copolymers of itaconic acid monoesters such as monomethyl itaconate, monoethyl itaconate, monopropyl itaconate, monobutyl itaconate and monoamyl itaconate.

Examples of comonomers for the above-described copolymers include acrylic acid esters such as methyl acrylate, ethyl acrylate, propyl acrylate, butyl acrylate, pentyl acrylate, amyl acrylate and hydroxyethyl acrylate, alkyl vinyl ethers such as methyl vinyl ether, ethyl vinyl ether, propyl vinyl ether and butyl vinyl ether, styrene, and p-hydroxystyrene.

The polycarboxylic acid derivative generally contains divalent groups derived from a compound having a combination of carboxyl groups and ethylenic-unsaturated double bonds as a repeating unit in the amount of approx. 10–90 molar %, and preferably approx. 30–60 molar %. The polycarboxylic acid derivative has the molecular weight in the range of approx. 30,000–5,000,000, and preferably in the range of approx. 50,000–1,000,000.

Particularly preferred polycarboxylic acids employable for producing the polycarboxylic acid derivatives of the present invention are the following polycarboxylic acids:

(1) methyl vinyl ether-maleic acid copolymer (50:50, polymerization ratio), molecular weight: approx. 300,000–900,000;

(2) styrene-maleic acid copolymer (50:50), molecular weight: approx. 50,000–200,000; and (3) maleic acid-butyl acrylate copolymer (50:50), molecular weight: approx. 50,000–200,000.

The above-described polycarboxylic acids are well known and prepared, for instance, by the following method.

A monomer containing a carboxyl group such as acrylic acid, maleic acid or maleic anhydride and one or more of other comonomers such as methyl vinyl ether, styrene and acrylic acid ester are introduced into a solvent such as water, methanol, ethanol, ethyl acetate, toluene, acetone or methyl ethyl ketone and nitrogen gas is introduced into the resulting solution. To the solution is then added a polymerization catalyst such as benzoyl peroxide or azobis(isobutylonitrile., and the mixture is heated under stirring to obtain a polycarboxylic acid.

Certain polycarboxylic acids are commercially available. Examples of the commercially available polycarboxylic acids include a variety of methyl vinyl ether maleic anhydride copolymers available from GAF, U.S.A. under the tradename of GANTREZ.

Details of processes for the preparation of polycarboxylic acids is described, for instance, in "Experimental Procedures for Vinyl Polymerization" (by Takayuki Ohtsu & Kiich Takemoto, published by Kyoritsu Publishing Co., Japan, 1964).

There is no specific limitation on the nonionic surface active agent to be attached to the polycarboxylic acid, as far as the nonionic surface active agent contains a hydroxyl group in the molecule. Preferred is a nonionic surface active agent having a repeating unit of the formula (II):

$$\text{-}(CH_2CH_2O)\text{-} \quad \text{(II)}$$

The above-described nonionio surface active agent particularly preferably has the formula (III):

$$R\text{-}(CH_2CH_2O)_nH \quad \text{(III)}$$

in which R is an alkyl group having 2–22 carbon atoms, an aryl group having an alkyl group of 4–12 carbon atoms as a substituent, an alkylcarbonyloxy group having an alkyl group of 9–19 carbon atoms, a sorbitane (1,4-anhydroglucitol or 1,5-anhydroglucitol) or sorbitol (glucitol) residue having at least one hydroxyl group esterified with a carboxylic acid having 2–22 carbon atoms; and n is an integer of 2–40.

Examples of the above-described nonionic surface active agent having the formula (III) include following compounds:

(1) polyoxyethylene alkyl ether (a compound having the formula (III) in which R is an alkyl group having 2–22 carbon atoms), for instance, a compound having an alkyl group such as ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, isopropyl, isobutyl or isoamyl, and 2–40 oxyethylene groups in a molecule;

(2) polyoxyethylene alkylphenyl ether (a compound having the formula (III) in which R is a phenyl group having an alkyl group of 4–12 carbon atoms of a substituent), for instance, a compound having an alkyl group such as pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, isobutyl or isoamyl, and 2–40 oxyethylene groups in a molecule;

(3) polyoxyethylene alkyl ester (a compound having the formula (III) in which R is an alkylcarbonyloxy group having an alkyl group of 9–19 carbon atoms), for instance, a compound having an alkyl group such as nonyl, decyl, undecyl, dodecyl, tridecyl, tetradecyl, pentadecyl, hexadecyl, heptadecyl, octadecyl, nonadecyl or eicosyl, and 2–40 oxyethylene groups in a molecule;

(4) aliphatic carboxylic acid ester of polyoxyethylene sorbitane (a compound having the formula (III) in which R is a sorbitane residue having at least one hydroxyl group esterified with an aliphatic carboxylic acid of 2–22 carbon atoms, for instance, a compound having a sorbitane residue esterified with one to three aliphatic carboxylic acids such as acetic acid, propionic acid, butyric acid, valeric acid, caproic acid, enanthic acid, caprylic acid, capric acid, undecylic acid, lauric acid, myristic acid, palmitic acid, stearic acid, oleic acid, arachic acid, behenic acid, isopropionic acid, isobutyric acid, isovaleric acid or isostearic acid, and 2–40 oxyethylene groups in a molecule;

(5) aliphatic carboxylic acid ester of polyoxyethylene sorbitol (a compound having the formula (III) in which R is a sorbitol residue having at least one hydroxyl group esterified with an aliphatic carboxylic acid of 2–22 carbon atoms), for instance, a compound having a sorbitol residue esterified with one to four aliphatic carboxylic acids such as acetic acid, propionic acid, butyric acid, valeric acid, caproic acid, enantic acid, caprylic acid, capric acid, undecylic acid, lauric acid, myristic acid, palmitic acid, stearic acid, oleic acid, arachic acid, behenic acid, isopropionic acid, isobutyric acid, isovaleric acid or isostearic acid, and 2–40 oxyethylene groups in a molecule; and (6) same compounds as the above-described compounds pounds (1) through (5) except that oxypropylene groups in the form of a block or random copolymer is contained in addition to the oxyethylene groups.

The acidic polymer can be employed in conjunction with a hydrophilic polymer such as gelatin or polyvinyl alcohol or an aqueous latex of a hydrophobic polymer. Further, the above-described polycarboxylic acid derivative can be employed as the acidic binder in conjunction with one or more polymers such as polystyrenesulfonic acid, poly(2-acrylamide-2-methylpropanesulfonic acid), polyacrylamide, poly-N-vinylpyrrolidone, hydroxyethylcellulose, hydroxypropylcellulose, ethylcellulose, carboxymethylcellulose, or agarose.

The porous reagent layer of the invention can contain a diazo-coupling accelerater, a surface active agent, and/or other additives, in addition to the diazonium salt and the acidic binder.

The diazonium salt, acidic binder and other additives can be incorporated into the porous reagent layer, for instance, by immersing the porous material into a solution containing these substances or by coating the solution substances over the porous material, and then drying the material. Otherwise, the solution containing these substances can be coated on a reagent layer integrally combined with an absorbent layer on a support, and the so treated integral element is dried.

The porous reagent layer of the invention (or, another porous reagent layer being optionally provided on the porous reagent layer defined in the invention) preferably contains a reaction accelerater to accelerate the reaction between the analyte and the diazonium salt.

The reactivity between bilirubin and a diazonium salt is prominently influenced by the solubility of the bilirubin. Since the free bilirubin (indirect bilirubin) of non-conjugate type is highly hydrophobic and poorly water soluble, the rate of reaction with a diazonium is low. In contrast, since the conjugate bilirubin and albumin-conjugated bilirubin are highly soluble in water, these rapidly reacts with a diazonium salt. Accordingly, the difference on the reaction rate residing between a variety of bilirubins is utilized to analyze separately each of the direct bilirubin (conjugate or protein-conjugated bilirubin) and the indirect bilirubin (free bilirubin).

The analytical element of the present invention can be employed in the same manner to separately analyze each of the direct and indirect bilirubins.

In the quantitative analysis of the total bilirubin content or a quick analysis of the indirect bilirubin, a reaction accelerator is necessarily included in the analytical element. The reaction accelerator employable for this purpose is known and described in a variety of texts. Examples of the accelerator include alcohols (e.g., methanol, ethanol, etc.), caffeine, sodium benzoate, sodium acetate, dyphylline (C. A. Registory No. [479-18-5]), urea, a nonionic surfactant, gum arabic, an acid, amide, sulfoxide, etc. The reaction accelerator can be optionally incorporated into the analytical element of the present invention.

There is no specific limitation on the support employable in the invention, so far as it allows transmission of light but not allows permeation of water. Such support is already known in the art. Examples of the support include transparent supports made of high-transparent synthetic resins such as polyethylene terephthalate, polycarbonate of bisphenol A, polystyrene, cellulose esters, and polyacrylates. The thickness of the support generally ranges from approx. 50 pm to approx. 2 mm, preferably from approx. 80 μm to approx. 300 μm.

As described hereinbefore, the multilayer analytical element of the present invention comprises the laminated structure of the porous reagent layer, the absorbent layer, and the support. These layers are preferably laminated in the order mentioned above. Further, the multilayer analytical element can further have one or more functional layers such as a spreading layer, an analyte(bilirubin, a conjugated complex between bilirubin and other substance, etc.) diffusion-preventing layer, or a light-blocking layer Accordingly, the multilayer analytical elements having such other layers are also embodiments of the invention.

The present invention is further described by the following examples.

EXAMPLE 1

An analytical element for quantitative analysis of bilirubin was prepared by superposing ah absorbent layer and a porous reagent layer successively on a support, using the following material and coating solutions.

(1) Support

Colorless transparent polyethylene terephthalate (PET) film (thickness: 180 μm)

(2) Absorbent Layer

| | |
|---|---|
| 50% Aqueous poly(2-hydxoy-3-oxypropylene)-n-nonylphenyl ether solution | 0.2 g. |
| Gelatin | 5 g |
| Water | 45 ml. |

This coating solution was coated over the support and dried to form an absorbent layer (thickness 10 μm, dry basis).

(3) Porous Reagent Layer

Formulation of diazonium salt solution

| | |
|---|---|
| 7-(2,3-Dihydroxypropyl)theophylline [479-18-5] | 5 g. |
| 5% Aqueous methyl vinyl ether-maleic anhydride (1:1, by molar ratio) coploymer solution | 5 ml. |

-continued

| | |
|---|---|
| (inherent viscosity: [η] = 1.0–1.4) | |
| Polyoxyethylene-p-t-octylphenyl ether (HLB = 13.5) | 0.1 g. |
| p-Sulfobenzendiazonium p-toluenesulfonate | 0.2 g. |
| Water | 45 ml. |

The above diazonium solution was incorporated into a membrane filter (Microfilter-300, mean pore size 3 || m, thickness 140 μm, void ratio 70%, available from Fuji Photo Film Co., Ltd., Japan) and dried to prepare a porous reagent layer sheet.

The microfilter containing the diazonium solution was pressed on the wetted absorbent layer to give an integral multilayer analytical element for quantitative analysis of total bilirubin.

Analysis of Bilirubin

The above-prepared analytical element was cut into a circular test piece (diameter 10 mm), and on the test piece were applied 10 μl. of commercially available control serums having different bilirubin contents, separately. The test pieces were incubated at 37° C. for 6 hours, and then measured on the color density formed thereon from the support side through a green filter at wavelength of approx. 530 nm. The results are set forth in Table 1.

TABLE 1

| Reflection (Optical) Density of Analytical Element | | | |
|---|---|---|---|
| Bilirubin Content of Control Serum (mg/dl) | | | |
| 0 | 5 | 10 | 20 |
| 0.35 | 0.57 | 0.72 | 0.91 |

EXAMPLE 2

The absorbent layer was provided on the PET sheet in the same manner in Example 1 except that the thickness of the absorbent layer was changed to 20 μm.

Diazonium salt solutions containing the following diazonium salts, respectively, were prepared in the same manner as in Example 1.

(1) 2,4-Dichlorobenzendiazonium tetrafluoroborate (2) 3,3-Dimethoxybiphenyl-4,4'-bisdizanium dichloride (3) p-Sulfobenzenediazonium benzenesulfonate The diazonium salt solution was incorporated into a broad cloth of 100 count cotton yarn and dried to prepare a porous reagent layer sheet. This sheet was laminated on the absorbent layer in the same manner as in Example 1, and cut to give a square piece (15 mm×15 mm). The resulting piece was inserted in a plastic mount in the manner as described in Japanese Patent provisional Publication No. 57(1982)-63452, to give a slide for quantitative analysis of bilirubin.

Analysis of Bilirubin

On the analytical slides were applied 10 μl. of a control serum (bilirubin content 20 mg/dl) per each. The slides were incubated at 37° C. for 6 hours, and then measured on the color density in the same manner as in Example 1. The results are set forth in Table 1.

TABLE 2

| Reflection Density of Analytical Element | | | |
|---|---|---|---|
| Diazonium salt | 1 | 2 | 3 |
| | 0.55 | 0.35 | 0.55 |

EXAMPLE 3

The procedure of Example 1 was repeated except that a coating layer (thickness 2 μm., dry basis) of agarose (Seaplaque. available from FMC Corp.) was provided on the absorbent layer, to give a multilayer analytical element for quantitative analysis of bilirubin.

The color density caused by fogging (color density observed in the absence of analyte) was measured at 450 nm for the analytical element. The resulting reflection density was 0.11, while the analytical element of Example 1 showed 0.22 of the color density caused by fogging. Thus, the color density caused by fogging decreased in the analytical element of Example 3.

Further, the color-formation sensitivity to bilirubin was the same as that in Example 1.

EXAMPLE 4

The procedure of Example 1 was repeated except that the acidic binder (methyl vinyl ether-maleic anhydride (1:1, by molar ratio) copolymer was employed in an aqueous solution of a concentration of 0, 0.5, 1.0, 1.5, 2.0, or 2.5 wt % in place of the 5% aqueous solution. Thus, six multilayer analytical elements were prepared.

On the analytical element were spotted Versatol P (total bilirubin content 18.6 mg/dl, containing direct bilirubin 3.8 mg/dl) and Omega high-bilirubin content control solution (total bilirubin content 10.9 mg/dl, containing 10.9 mg/dl), respectively. The color density formed thereon was then measured in the same manner as in Example 1. The results are set forth in Table 3.

TABLE 3

| Reflection Density of Analytical Element | | | | | |
|---|---|---|---|---|---|
| Concentration of Acidic Binder (wt. %) | | | | | |
| 0 | 0.5 | 1.0 | 1.5 | 2.0 | 2.5 |
| Control Liquid: Versatol P | | | | | |
| 0.60 | 0.72 | 0.73 | 0.71 | 0.70 | 0.60 |
| Control Liquid: Omega high-bilirubin content | | | | | |
| 0.68 | 0.75 | 0.76 | 0.74 | 0.73 | 0.68 |

The above results indicate that the above-mentioned diazonium salts show color formation corresponding to the total bilirubin content in the liquid sample, the color formation depending upon the content of the acidic binder.

EXAMPLE 5

5 ml. of 15 wt. % aqueous solution of divinylbenzene(dimethylamino)ethylacrylate copolymer latex was added to the coating solution for the preparation of the absorbent layer. The resulting mixture was coated on the PET support, and dried to give an absorbent layer (thickness 15 μm, dry basis).

A diazonium salt solution was prepared in the same manner as in Example 1 except that the methyl vinyl ether-maleic anhydride copolymer was replaced with the same amount of poly(4-sulfoethylene) having an average molecular weight of approx. 340,000. Thereafter, the same procedure was performed as in Example 1 to form a porous reagent layer and then an integral multilayer analytical element was prepared.

The bilirubin analysis described in Example 1 was repeated on the above-mentioned analytical element. The results were almost same as the results of Example 1.

EXAMPLE 6

An absorbent layer (thickness 15 μm) was formed by coating and drying the same coating solution (for the absorbent layer) as in Example 5 over the PET support. On the absorbent layer was coated an aqueous polyvinyl alcohol and dried to give a bilirubin diffusion-preventing layer (thickness 1 μm).

Independently, a membrane filter of blushed polymer made of cellulose acetate (thickness 140 μm, mean pore size 1.2 μm, void ratio 70%) was impregnated with the following diazonium salt solution, and dried.

Formulation of diazonium salt solution

| | |
|---|---|
| 2-Methoxy-5-tetradecyloxycarbonylbenzene diazonium tetrafluoreborate | 7.5 g. |
| Ethanol | 1 g. |
| Acetone | 0.45 g. |
| Aqueous solution of 0.5% poly(2-hydroxy-3-oxypropylene)- n-nonylphenyl ether & 5% methyl vinyl ether-maleic anhydride (1:1, by molar ratio) coploymer | 10 g. |
| Diphylline | 10 g. |
| Water | 100 ml. |

The so treated membrane filter was pressed on the bilirubin diffusion-preventing layer under wet conditions and dried to give an integral multilayer analytical element. The element was then inserted in a plastic mount to prepare a slide for quantitative analysis of bilirubin.

On the analytical element were spotted 10 μl. of serum having different bilirubin contents. After incubation at 37° C. for 6 min,.the color formation was measured by reflection photometry from the support side at 550 nm. The results are set forth in Table 4.

TABLE 4

| Reflection Density of Analytical Element Total Bilirubin Content of Control Serum (mg/dl) | | |
|---|---|---|
| 0.6 | 10 | 19 |
| 0.16 | 0.45 | 0.63 |

The coating solution set forth below was coated on the same PET support as in Example 1 and dried at 95° C. for 1 hour to form an absorbent layer of thickness 20 μm (dry basis).

Formulation of the coating layer

| | |
|---|---|
| Polyvinyl alcohol (saponification degree 88%, average M.W. 500) | 10 g. |
| Dimethylolurea | 0.3 g. |
| Polyoxyethylene octylphenyl ether (mean polymerization degree of polyoxyethylene 9–10) | 0.2 g. |
| Water to make | 100 ml. |

Independently, the same diazonium salt solution as in Example but containing 2 g. of particulate titanium dioxide (mean particle size 0.4 μm.) was prepared.

The above-mentioned absorbent layer was wetted with water at 25° C. and immediately pressed on a broad cloth of 100 count cotton yarn. The wet element was dried. The broad cloth of the element was subsequently impregnated with the above diazonium salt solution containing the solid particles and dried to prepare a porous reagent layer. Thus, an integral multilayer analytical element was prepared. The element was then inserted into a mount in the same manner as in Example 2 to give a slide for quantitative analysis of bilirubin.

The above analytical slide was subjected to bilirubin analysis in the same manner as in Example 1, to give the results set forth in Table 5. The results indicated that the quantitative analysis of bilirubin can be accomplished by the use of the above-mentioned integral multilayer analytical element.

TABLE 5

| Reflection Density of Analytical Element Bilirubin Content of Control Serum (mg/dl) | | | |
|---|---|---|---|
| 0 | 5 | 10 | 20 |
| 0.21 | 0.37 | 0.49 | 0.69 |

We claim:

1. A multilayer analytical element for quantitative analysis of bilirubin in a liquid sample which comprises, in this order, (1) a porous reagent layer containing an acidic binder and a diazonium salt being reactive to bilirubin to produce azobilirubin;

(2) an absorbent layer comprising a hydrophilic polymer capable of absorbing a solvent in a liquid sample without accepting bilirubin in a liquid sample diffusing into said porous reagent layer; and (3) a liquid-impermeable light-transmissive support.

2. The analytical element claimed in claim 1, in which said absorbent layer comprises a hydrophilic polymer having a degree of swelling in water at 30° C. in the range of 1.5 to 30 times as much as its original volume.

3. The analytical element claimed in claim 1 or 2, in which said absorbent layer contains a basic polymer.

4. The analytical element claimed in claim 3, in which said basic polymer is:

a homopolymer of an unsaturated monomer selected from the group consisting of 2-vinylpyridine, 4-vinylpyridine, N-vinylimidazole, 1-vinyl-3-alkyl-2,3-dihydroimidazole, 2-vinyl-1-alkyl-imidazole, (dialkylamino)alkyl acrylate, (dialkylamino) alkyl methacrylate, N-[(dialkylamino)alkyl]acrylamide, and N-[(dialkylamino)alkyl]methacrylamide;

a copolymer of said unsaturated monomers; or a copolymer of said unsaturated monomer and other unsaturated monomer than said unsaturated monomer.

5. The analytical element claimed in claim 1 or 2, in which said acidic binder is:

a homopolymer of unsaturated monomer selected from the group consisting of p-styrenesulfonic acid, acrylic acid, methacrylic acid, maleic acid, maleic anhydride, maleic acid monoamide, maleic acid monoester, N-(sulfoalkyl)acrylamide, and N-(sulfoalkyl)methacrylamide;

a copolymer of said unsaturated monomers; or a copolymer of said unsaturated monomer and other unsaturated monomer than said unsaturated monomer.

6. The analytical element as claimed in claim 1 wherein the absorbent layer comprises a material selected from the group consisting of gelatin, dextran, starch, modified starch, hydroxyethyl-modified agarose, polyvinyl alcohol, a homopolymer of hydroxyethyl acrylate, a homopolymer of hydroxyethyl methacrylate, a homopolymer of N-(hydroxyalkyl)acrylamide, and copolymers of acrylamide with one or more monomers selected from the group consisting of hydroxyethyl acrylate, hydroxyethyl methacrylate and N-(hydroxyalkyl)-acrylamide.

7. The analytical element as claimed in claim 1 which further contains a light-blocking layer.

8. A multilayer analytical element for quantitative analysis of bilirubin in a liquid sample which comprises, in this order, (1) a porous reagent layer containing an acidic binder and a diazonium salt being reactive to bilirubin to produce azobilirubin;
(2) a layer for presenting diffusion of bilirubin;
(3) an absorbent layer comprising a hydrophilic polymer capable of absorbing a solvent in a liquid sample without accepting bilirubin in a liquid sample diffusing into said porous reagent layer; and
(4) a liquid-impermeable light-transmissive support.

* * * * *